US012661434B2

(12) United States Patent (10) Patent No.: US 12,661,434 B2

Farrell (45) Date of Patent: Jun. 23, 2026

(54) HYDROPHILIC COATINGS FOR MEDICAL DEVICES

(71) Applicant: Hollister Incorporated, Libertyville, IL (US)

(72) Inventor: David J. Farrell, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 1295 days.

(21) Appl. No.: 17/415,638

(22) PCT Filed: Dec. 12, 2019

(86) PCT No.: PCT/US2019/065938

§ 371 (c)(1),
(2) Date: Jun. 17, 2021

(87) PCT Pub. No.: WO2020/131561

PCT Pub. Date: Jun. 25, 2020

(65) Prior Publication Data

US 2022/0054718 A1    Feb. 24, 2022

Related U.S. Application Data

(60) Provisional application No. 62/781,987, filed on Dec. 19, 2018.

(51) Int. Cl.
| | |
|---|---|
| *A61L 29/12* | (2006.01) |
| *A61L 29/14* | (2006.01) |
| *C08L 39/06* | (2006.01) |

(52) U.S. Cl.
CPC ............. *A61L 29/126* (2013.01); *A61L 29/14* (2013.01); *C08L 39/06* (2013.01); *A61L 2400/10* (2013.01); *A61L 2420/04* (2013.01)

(58) Field of Classification Search
CPC . C08L 39/06; B32B 1/02; B32B 27/32; Y10T 428/1352; Y10T 428/31725
See application file for complete search history.

(56) References Cited

U.S. PATENT DOCUMENTS

| | | | |
|---|---|---|---|
| 3,169,527 A | 2/1965 | Sheridan | |
| 3,556,294 A | 1/1971 | Walck et al. | |
| 4,186,745 A | 2/1980 | Lewis et al. | |
| 4,417,892 A | 11/1983 | Meisch | |
| 4,898,734 A | 2/1990 | Mathiowitz et al. | |
| 4,906,237 A * | 3/1990 | Johansson ............... A61L 29/14 |
| | | | 604/265 |
| 5,331,027 A * | 7/1994 | Whitbourne ............ A61L 27/34 |
| | | | 525/182 |

(Continued)

FOREIGN PATENT DOCUMENTS

| | | |
|---|---|---|
| CN | 106084398 A | 11/2016 |
| CN | 106674748 A | 5/2017 |

(Continued)

OTHER PUBLICATIONS

International Search Report and Written Opinion for International Application No. PCT/US2019/065938, dated Mar. 30, 2020.

*Primary Examiner* — Thomas J Kessler

(74) *Attorney, Agent, or Firm* — Cook Alex Ltd.

(57) ABSTRACT

Hydrophilic coatings including a polymer matrix having voids wherein microparticles having a lubricious liquid are located within the voids.

20 Claims, 2 Drawing Sheets

(56)            References Cited

U.S. PATENT DOCUMENTS

| | | | |
|---|---|---|---|
| 5,657,833 | A | 8/1997 | Freeman |
| 6,318,139 | B1 * | 11/2001 | Ishikura ............... C10M 129/40 |
| | | | 72/42 |
| 2002/0136770 | A1 * | 9/2002 | Quong ................... A61K 8/342 |
| | | | 424/407 |
| 2005/0123758 | A1 | 6/2005 | Ghasripoor et al. |
| 2005/0127610 | A1 | 6/2005 | Pratesi et al. |
| 2009/0299334 | A1 | 12/2009 | Nishtala et al. |
| 2010/0268191 | A1 | 10/2010 | Trudel et al. |
| 2012/0302471 | A1 * | 11/2012 | Webb ................... C08G 18/765 |
| | | | 508/103 |
| 2013/0186778 | A1 | 7/2013 | Terry |
| 2015/0040943 | A1 | 2/2015 | Dunn |
| 2016/0032074 | A1 | 2/2016 | Aizenberg et al. |

FOREIGN PATENT DOCUMENTS

| | | | | |
|---|---|---|---|---|
| CN | 107779557 | A | * | 3/2018 |
| JP | 0297596 | A | * | 4/1990 |
| JP | H0297596 | A | * | 4/1990 |
| RU | 2657608 | C1 | * | 6/2018 |
| WO | WO-9858990 | A1 | * | 12/1998 |
| WO | 2003055964 | | | 7/2003 |
| WO | 2013058660 | A1 | | 4/2013 |
| WO | 2014209441 | A2 | | 12/2014 |
| WO | 2017146976 | A1 | | 8/2017 |
| WO | 2018013805 | A2 | | 1/2018 |

* cited by examiner

HYDROPHILIC COATINGS FOR MEDICAL DEVICES

The present application is the U.S. National Stage Application of PCT Application No. PCT/US2019/065938, filed Dec. 12, 2019, which claims the benefit and priority of U.S. Provisional Patent Application No. 62/781,987, filed Dec. 19, 2018, both of which are hereby incorporated herein by reference.

TECHNICAL FIELD

The present disclosure generally relates to hydrophilic coatings that include a hydrophilic polymer matrix having voids in the matrix wherein microparticles including a lubricating liquid are located in the voids of the matrix. Furthermore, the present disclosure relates to medical devices having such hydrophilic coatings applied thereto and a method for making medical devices having such hydrophilic coatings thereon.

BACKGROUND

It is desirable for medical devices that are inserted into the body to have a lubricated or lubricious outer surface to facilitate insertion into and/or removal from the body. Such devices may include, for example, urinary catheters, endoscopes, cardiovascular catheters, syringes, vascular stents, etc. Such medical devices may have a lubricant gel placed on the outer surface of the device or may have a hydrophilic coating or layer disposed on the outer surface of the device. Hydrophilic coatings are becoming the preferred method of providing a lubricious surface because of their high lubricity and ease of use. Hydrophilic coatings become slippery or lubricous when lubricated with a liquid, such as saline or water. The lubricous hydrophilic coating eases insertion and removal of the device, minimizes soft tissue damage and reduces overall discomfort during use of the medical device.

When a medical device having a hydrophilic coating is used, the hydrophilic coating is typically hydrated for a certain period of time prior to use to activate the hydrophilic coating. For example, the user may immerse or otherwise contact the hydrophilic coating with a liquid to wet or activate the coating. In some instances, the medical device is packaged in a packaging that includes liquid or water vapor within the package that hydrates the coating while the device is in the package so that the device is ready to use right out of the package. Hydrophilic coatings do have some issues, which may include the time period required for hydration prior to use and some hydrophilic coatings may dry-out prior or during use. Dry-out occurs when the hydration fluid evaporates from the hydrophilic coating, rending the coating less lubricious. In some instances, after dry-out, the surface of the coating becomes sticky.

There remains a need for improved hydrophilic coatings.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect of the present disclosure, a lubricious hydrophilic coating includes a hydrophilic polymer matrix having voids, and microparticles comprising a lubricating liquid located in the voids of the hydrophilic polymer matrix.

In another aspect, a medical device having a hydrophilic coating includes a medical device including a surface and a hydrophilic coating disposed on the surface of the medical device, the hydrophilic coating comprises a hydrophilic polymer matrix having voids and microparticles comprising a lubricating liquid located in the voids of the hydrophilic polymer matrix.

In another aspect, a method of making a medical device having a hydrophilic coating includes applying a hydrophilic coating formulation to a surface of the medical device. The hydrophilic coating formulation comprises a hydrophilic polymer and microparticles comprising a lubricating liquid or a microparticle precursor. A hydrophilic coating is formed on the surface of the medical device from the hydrophilic coating formulation, wherein the hydrophilic coating includes a matrix having voids and microparticles comprising lubricating liquid are located in the voids.

DETAILED DESCRIPTION

The present disclosure relates to lubricious hydrophilic coatings and devices having such coatings thereon. The hydrophilic coatings may be applied to surfaces of medical devices. Such medical devices may include shafts or tubes that may be inserted into and advanced within a lumen of a body, such as a urethra, esophagus, or fallopian tube. Such medical devices include urinary catheters, endovascular catheters, endoscopes, exploratory and biopsy devices, etc. While some of the embodiments set forth below may be described in the context of urinary catheters, the disclosure is not limited to such and the features disclosed herein may be applicable to any medical tubing that is inserted into a body lumen.

Figures 1, 2, 3:
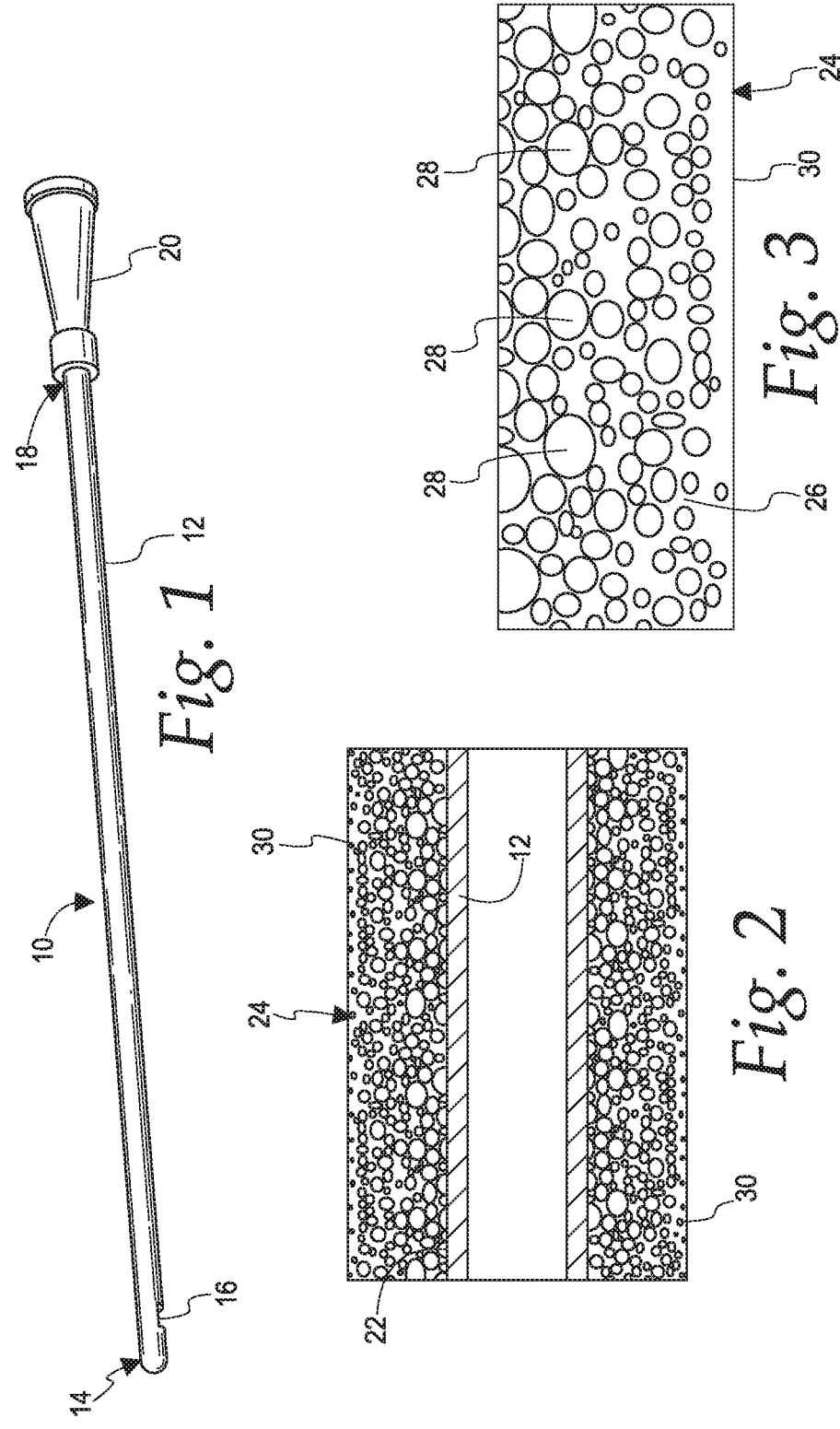
FIG. 1 is a perspective view of a urinary catheter having a hydrophilic coating thereon.
FIG. 2 is a cross-sectional view of the urinary catheter of FIG. 1.
FIG. 3 is an enlarged cross-sectional view of a portion of the hydrophilic coating.

An exemplary urinary catheter 10 according to the present disclosure is shown in FIG. 1. The catheter 10 includes a catheter shaft 12. A proximal end 14 of the catheter shaft 12 includes one or more draining holes or eyes 16 for the drainage of bodily fluids therethrough and into an internal conduit or lumen of the catheter shaft 12. The distal end 18 of the catheter shaft 12 may include a connecting member 20, such as a funnel, for fluidly connecting the catheter 10 to a collection container, such as a collection bag into which urine drains.

Referring to FIG. 2, the catheter shaft 12 includes a surface 22 having a hydrophilic coating 24 thereon. For example, the surface 22 may be an outer surface of the catheter shaft 12. In other medical devices, the surface having the coating may be an inner surface, depending on the medical device and desired use. FIG. 3 is an enlarged cross-sectional view of an exemplary portion of the hydrophilic coating 24. The hydrophilic coating 24 may include a polymer matrix 26 having voids that include microparticles 28 located in the voids. The microparticles 28 may be microcapsules or micelles. The microparticles 28 may include a liquid lubricant, such as water or an oleic composition. When the microparticles 28 in include water, the water may optionally include additives, such as osmolality increasing additives. The microparticles 28 release the liquid lubricant, which migrates to the outer surface 30 of the coating 28 to render the coating lubricious. In one embodiment, the microparticles 28 may release the liquid lubricant when the coating 24 is placed under a particular condition. For example, the microparticles 28 may rupture or burst to release liquid when a compression force is placed on the coating 24. In another embodiment, the microparticles 28 may be solid materials that melt when exposed to ambient temperatures (ambient temperature being 21° C.-25° C.). For instance, the microparticles may be ice or solidified oils which melt within the matrix at ambient temperatures.

In one embodiment, the microparticles 28 may be microcapsules filled with the liquid lubricant. For example, the microcapsules may be formed having a polymeric capsule wall made of, for example, shellac (evaporative formation), cyanoacrylate (reactive), alginate (reactive), wax (melt), cellulose, agar or other polysaccharides or other suitable shell wall that are filled with the liquid. In another embodiment, the microparticles 28 may be micelles formed from gel forming polymers including gellan gum and the liquid lubricant.

For example, the microparticles 28 may include a gelling agent or hydrocolloid and the liquid lubricant. The gelling agent or hydrocolloid may be, but is not limited to, a polysaccharide, which may be gellan gum, agar, alginate or xanthan gum and mixtures thereof, or other suitable polysaccharide hydrocolloids.

In one embodiment, the microparticles 28 may be formed of gellan gum and water. The gellan gum microparticles may be microgels, which may be microgel packs, having a size of less than 3 microns (μm). In other embodiment, the microgels may be larger. The microgels may be in the form of a capsule or micelles.

Figure 4:
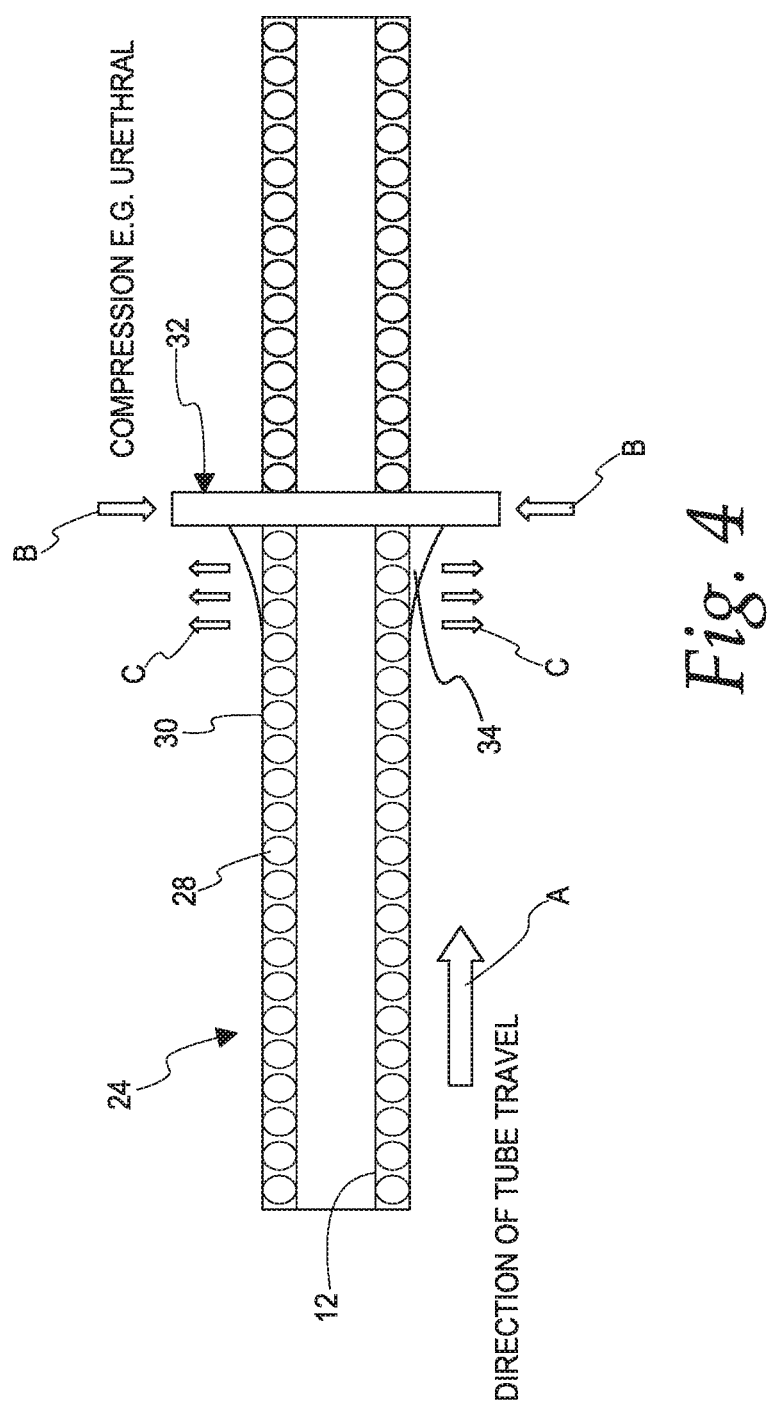
FIG. 4 is a schematic illustration of a urinary catheter during use.

FIG. 4 is a schematic representation of a catheter shaft 12 being inserted into a urethra 32. The catheter 12 is being inserted into the urethra 32 in the direction of arrow A. The urethra 32 exerts a compression force, represented by arrows B, on the coating 24 of the catheter. The compression force B causes the microparticles 28 to rupture releasing the lubricating liquid 34. The lubricating liquid 34 migrates to or extrudes from the outer surface 30 of the hydrophilic coating 24, thereby rendering the coating lubricious. In embodiment, the microparticles are microgels formed from gellan gum and water. When a compression force is exerted on the coating 24, the microgels rupture releasing the water.

Some medical devices are exposed to radiation for various reasons during manufacturing and packaging. For example, urinary catheters may be exposed to sterilizing radiation. Such sterilizing radiation may include exposure to gamma or E-beam radiation. Exposure to radiation may degrade or weaken the microparticles such that the microparticles more readily release the lubricating liquid. For example, when the microparticles are microgels made from a hydrocolloid, such a gellan gum, and water, the microgels may be degraded or weaken by exposure to radiation. This degradation or weakening of the microgels causes the microgels to more easily rupture, which in turn results in the microgels more readily releasing the lubricating liquid. For example, when a compressive force is applied to the coating, the degraded microgels more easily rupture to release the liquid.

Furthermore, when the microparticles are made from a hydrocolloid, such as gellan gum, and water, the hydrophilic coating is less likely to dry out during use because of the affinity between the hydrocolloid and water may slow the evaporation process. Thus, less water will evaporate from the hydrophilic coating during a given time period.

Microparticle precursors may be added to the hydrophilic coating formulation. For example, microparticle precursors, such as particles of gellan gum in the dry state, may be added directly to a hydrophilic coating formulation, which is applied to a surface to form a hydrophilic coating thereon. When kept in suspension, by any means, hydrophilic coatings can be formed, and particularly PVP based hydrophilic coatings can be formed, which contain particles of gellan gum dispersed throughout the coating. The hydrophilic formulation can be dried and cured in the manner typical for forming the hydrophilic formulation into a hydrophilic coating. Once formed, the hydrophilic coating may be hydrated thus causing the particles of gellan gum within the coating to swell, thereby forming hydrated microparticles containing water. In one embodiment, the gellan gum is entrained within a continuous phase of the hydrophilic polymer, such as a continuous phase of polyvinylpyrrolidone. The water swollen particles of gellan gum are now a hydrogel particle or region entrained within a hydrated hydrogel or hydrophilic coating. The gellan gel particles may be softened or broken down to an effectively liquid phase by subjecting the hydrated hydrophilic coating by exposure to such radiation as gamma radiation or e-beam. Such sources of radiation can also be used for sterilization of medical devices. The regions containing the gellan gum and water are entrained or encapsulated within the continuous hydrophilic coating.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A lubricious hydrophilic coating on a medical device, comprising:
   a cured hydrophilic polymer forming a hydrophilic coating on the medical device, the cured hydrophilic polymer comprising an outer surface and a matrix having voids; and
   microparticles comprising a polysaccharide and water, the microparticles located in the voids of the matrix of the cured hydrophilic polymer, the microparticles configured to release the water, wherein the water migrates to the outer surface of the hydrophilic coating and the water hydrates the hydrophilic coating, thereby rendering the hydrophilic coating lubricious.

2. The lubricious hydrophilic coating on the medical device of claim 1, wherein the microparticles comprise microcapsules.

3. The lubricious hydrophilic coating on the medical device of claim 1, wherein the microparticles comprise micelles.

4. The lubricious hydrophilic coating on the medical device of claim 1, wherein the water includes an additive.

5. The lubricous hydrophilic coating on the medical device of claim 4, wherein the additive comprises an osmolality increasing additive.

6. The lubricious hydrophilic coating on the medical device of claim 1, wherein the polysaccharide is a gelling agent.

7. The lubricious hydrophilic coating on the medical device of claim 1, wherein the polysaccharide is a hydrocolloid.

8. The lubricious hydrophilic coating on the medical device of claim 1, wherein the polysaccharide comprises gellan gum.

9. The lubricious hydrophilic coating on the medical device of claim 8, wherein the microparticles comprise microgels.

10. The lubricious hydrophilic coating on the medical device of claim 1, wherein the cured hydrophilic polymer comprises polyvinylpyrrolidone.

11. The lubricious hydrophilic coating on the medical device of claim 1, wherein the microparticles release the water upon a compression force being applied to an outer surface of the hydrophilic coating.

12. The lubricious hydrophilic coating on the medical device of claim 1, wherein the water migrates to an outer surface of the hydrophilic coating upon a compression force being applied to the outer surface of the hydrophilic coating.

13. The lubricious hydrophilic coating on the medical device of claim 1, wherein the medical device comprises a urinary catheter.

14. The lubricious hydrophilic coating on the medical device of claim 13, wherein the urinary catheter comprises a catheter shaft having a surface and the hydrophilic coating is located on the surface.

15. A lubricious hydrophilic coating on a urinary catheter, comprising:

a cured hydrophilic polymer forming a hydrophilic coating on the urinary catheter, the cured hydrophilic polymer comprising an outer surface and a matrix having voids; and microparticles comprising a polysaccharide and water, the microparticles located in the voids of the matrix of the cured hydrophilic polymer, the microparticles configured to release the water, wherein the water migrates to the outer surface of the hydrophilic coating and the water hydrates the hydrophilic coating, thereby rendering the hydrophilic coating lubricious.

16. The lubricious hydrophilic coating on the urinary catheter of claim 15, wherein the microparticles comprise microcapsules.

17. The lubricious hydrophilic coating on the urinary catheter of claim 15, wherein the microparticles comprise micelles.

18. The lubricious hydrophilic coating on the urinary catheter of claim 15, wherein the polysaccharide is a gelling agent.

19. The lubricious hydrophilic coating on the urinary catheter of claim 15, wherein the polysaccharide is a hydrocolloid.

20. The lubricious hydrophilic coating on the urinary catheter of claim 15, wherein the polysaccharide comprises gellan gum.

* * * * *